US009946057B2

(12) United States Patent
Hufnagel et al.

(10) Patent No.: US 9,946,057 B2
(45) Date of Patent: Apr. 17, 2018

(54) MICROSCOPE MODULE FOR A MICROSCOPE ARRANGEMENT FOR IMAGING A SAMPLE

(71) Applicant: European Molecular Biology Laboratory, Heidelberg (DE)

(72) Inventors: Lars Hufnagel, Mauer (DE); Jan Ellenberg, Heidelberg (DE); Uros Krzic, Heidelberg (DE); Petr Strnad, Marianske Lazne (CZ)

(73) Assignee: European Molecular Biology Laboratory, Heidelberg (DE)

( * ) Notice: Subject to any disclaimer, the term of this patent is extended or adjusted under 35 U.S.C. 154(b) by 0 days.

(21) Appl. No.: 14/785,624

(22) PCT Filed: May 7, 2014

(86) PCT No.: PCT/EP2014/059307
§ 371 (c)(1),
(2) Date: Oct. 19, 2015

(87) PCT Pub. No.: WO2014/180884
PCT Pub. Date: Nov. 13, 2014

(65) Prior Publication Data
US 2016/0070091 A1 Mar. 10, 2016

(30) Foreign Application Priority Data
May 10, 2013 (EP) ..................... 13167360

(51) Int. Cl.
*G02B 21/06* (2006.01)
*G02B 21/00* (2006.01)
(Continued)

(52) U.S. Cl.
CPC ......... *G02B 21/06* (2013.01); *G01N 21/6458* (2013.01); *G02B 21/0076* (2013.01);
(Continued)

(58) Field of Classification Search
CPC .. G02B 21/00; G02B 21/0004; G02B 21/002; G02B 21/0032; G02B 21/06;
(Continued)

(56) References Cited

U.S. PATENT DOCUMENTS

| 5,969,854 A | 10/1999 | Stelzer et al. |
| 7,554,725 B2 | 6/2009 | Stelzer et al. |

(Continued)

FOREIGN PATENT DOCUMENTS

| DE | 4326473 A1 | 9/1995 |
| EP | 1777572 A1 | 4/2007 |

(Continued)

OTHER PUBLICATIONS

J. Huisken, D. Y. R. Stainier, 'Selective plane illumination microscopy techniques in developmental biology', Development, vol. 136, pp. 1963-1975.*

(Continued)

*Primary Examiner* — Arnel C Lavarias
(74) *Attorney, Agent, or Firm* — 24IP Law Group; Timothy R DeWitt

(57) ABSTRACT

A microscope module (300) for imaging a sample (270) is disclosed. The microscope module (300) includes at least one illumination objective (210) for producing an illumination beam along an illumination beam path (215) arranged to illuminate lower surface of the sample (270) and at least one detection objective (220) having a detection path (225). The detection path (225) is at an angle to the illumination beam path (215).

13 Claims, 4 Drawing Sheets

(51) Int. Cl.
*G01N 21/64* (2006.01)
*G02B 21/16* (2006.01)
*G02B 21/34* (2006.01)
*G02B 21/36* (2006.01)
*G02B 21/02* (2006.01)
*G02B 21/33* (2006.01)

(52) U.S. Cl.
CPC ......... *G02B 21/0088* (2013.01); *G02B 21/02* (2013.01); *G02B 21/16* (2013.01); *G02B 21/33* (2013.01); *G02B 21/34* (2013.01); *G02B 21/367* (2013.01)

(58) Field of Classification Search
CPC ........ G02B 21/24; G02B 21/26; G02B 21/33; G02B 21/34; G02B 21/0076
USPC ....... 359/385, 362, 363, 368, 369, 388, 390, 359/391, 396, 398, 433
See application file for complete search history.

(56) References Cited

U.S. PATENT DOCUMENTS

| | | |
|---|---|---|
| 2006/0274424 A1 | 12/2006 | Okazaki et al. |
| 2009/0174937 A1* | 7/2009 | Holy ............... G02B 21/08 359/382 |
| 2009/0231689 A1 | 9/2009 | Pittsyn et al. |
| 2012/0320438 A1 | 12/2012 | Knebel et al. |
| 2016/0139394 A1* | 5/2016 | Taniguchi ......... G02B 21/24 359/385 |

FOREIGN PATENT DOCUMENTS

| | | |
|---|---|---|
| EP | 2983029 A1 | 2/2016 |
| JP | H11513145 | 11/1999 |
| JP | A 2005195792 | 7/2005 |
| JP | A 2013003585 | 2/2006 |
| JP | A 2013003585 | 1/2013 |
| JP | 2014202967 | 10/2014 |
| WO | 2004053558 A1 | 6/2004 |
| WO | 2006009212 A1 | 1/2006 |
| WO | 2012122027 A2 | 9/2012 |

OTHER PUBLICATIONS

A. Kaufmann et. al., :Multilayer mounting enables long-term imaging of zebrafish development in a light sheet microscope, Development 139, pp. 3242-3247 (2012).
J. Huisken, "Slicing embryos gently with laser light sheets," Bioessays 34, pp. 406-411 (2012).
P. J. Keller et al., "Three-dimensional preparation and imaging reveal intrinsic microtubule properties," Nature Methods vol. 4, No. 10, pp. 843-846 (2007).
M. Weber and J. Huisken, "Light sheet microscopy for real-time developmental biology," Current Opinion in Genetics and Development 21:566-572 (2011).
Y. Wu et. al., "Inverted selsective plane illumination microscopy (iSPIM) enables coupled cell identity lineaging and neurodevelopmental imaging in Caenorhabditis elegans," PNAS, vol. 108, No. 43, pp. 17708-17713 (2011).
C. J. Engelbrecht et. al., "Three-dimensional laser microsurgery in light-sheet based microscopy (SPIM)," Optics Express, vol. 15, No. 10, 6420-6425 (2007).

* cited by examiner

MICROSCOPE MODULE FOR A MICROSCOPE ARRANGEMENT FOR IMAGING A SAMPLE

CROSS-REFERENCE TO RELATED APPLICATIONS

None

FIELD OF THE INVENTION

The field of the invention relates to a microscope module for imaging a sample.

BACKGROUND OF THE INVENTION

Selective Plane Illumination Microscopy (SPIM) is a technology that employs generation of a light sheet to illuminate a sample and a perpendicular detection system to enable imaging of optical sections of the samples, which can be living or not. In most embodiments, the SPIM system requires extensive sample preparation to hold the sample in a correct position for imaging. For example, the sample is typically embedded in an agarose cylinder which is submerged in a small chamber filled with an immersion medium, such as water. The technique has been known for over a hundred years, but has only recently found extensive application in imaging biological samples. One disadvantage with the technique is that agarose is not compatible with all biological specimens. The samples are also embedded in vertical cylinders of agarose of limited height in current SPIM systems. This arrangement does not allow for access to the sample during imaging or re-positioning of the sample. The arrangement limits the number of samples that can be imaged since, for example, it is not possible to stack 50 samples in the limited length of the agarose cylinder.

SPIM systems are described, for example, in international patent application No. WO 2004/053558 (Stelzer et al., assigned to the European Molecular Biology Laboratory). This disclosure teaches a microscope in which a thin strip of light (light sheet) illuminates a sample (specimen) and the sample is viewed through a detector. The axis of the detector is situated substantially perpendicular to the direction of an illumination beam. The sample is displaced through the strip of light and the detector records diffused light from the sample or fluorescent light from the sample in a series of images. Three-dimensional images of the sample can be created by the optical sectioning of the sample and then reconstructing the entire image of the sample.

Shroff et al have developed a module for a conventional microscope that is coupled to the translational base of the conventional microscope (International Patent Application No. WO 2012/122027, Shroff et al, assigned to the US). The combination of the module and an inverted microscope enables the same sample to be imaged in two ways that can complement each other.

SUMMARY OF THE INVENTION

A microscope module for imaging one or more samples is disclosed. The microscope module comprises an illumination device for producing an illumination beam along an illumination beam path and at least one detection device having a detection path. The illumination beam is arranged to illuminate lower surfaces of one or more of the samples. The illumination beam path is arranged at an angle to the detection path. In one aspect of the disclosure, the angle is substantially orthogonal. The samples are placed in a culture medium. There is no need to mount the samples in a solid or viscous mounting media which might be incompatible with the survival of biological samples and also complicates retrieval and manipulation of the samples.

The sample is placed in a sample holder. The bottom of the sample holder is at least partially transparent to the illumination beam, so that the illumination beam can illuminate the sample. One example of such transparent bottoms is a membrane. The sample holder comprises at least one protrusion in which the sample is held. In one aspect of the disclosure, the protrusion may be in the form of an elongated trough in which a plurality of the samples are held in a culture medium.

The sample holder is arranged to enable easy removal from the microscope module. This enables the samples to be cultured in the sample holder outside of the microscope module and then placed undisturbed into the microscope module for imaging.

The arrangement of this disclosure enables the illumination objective and the detection objective to be placed in an immersion medium that is separate from the culture medium in which the samples are placed. The separation of the culture medium from the immersion medium helps to maintain sterility and also enables the use of small volumes of culture media. The transparent bottom, the immersion medium and the culture medium have substantially the same refractive index to minimise optical aberrations.

The disclosure also teaches a method of imaging a plurality of samples that comprises arranging an illumination objective to illuminate lower surfaces of the plurality of the samples and arranging a detection objective to detect light emitted from the plurality of samples at an approximately orthogonal angle to the illumination beam path. The detected light can be used to create an image of one or more of the plurality of samples.

DETAILED DESCRIPTION OF THE INVENTION

The invention will now be described on the basis of the drawings. It will be understood that the embodiments and aspects of the invention described herein are only examples and do not limit the protective scope of the claims in any way. The invention is defined by the claims and their equivalents. It will be understood that features of one aspect or embodiment of the invention can be combined with a feature of a different aspect or aspects and/or embodiments of the invention.

Figure 1:
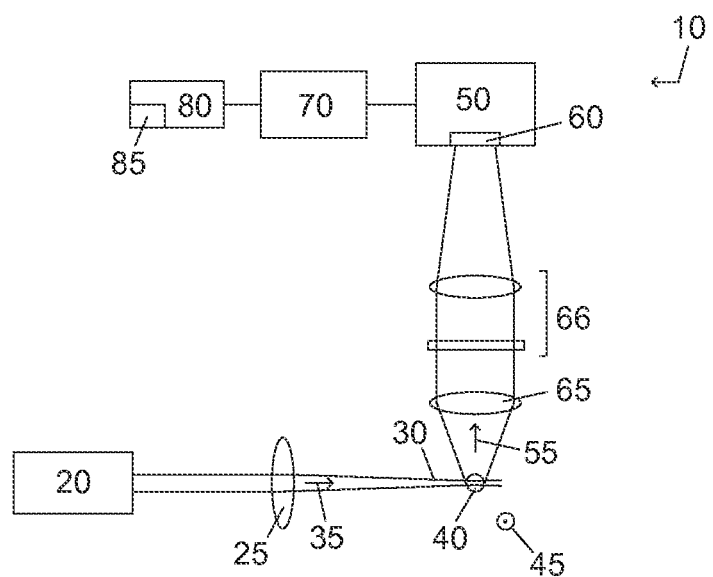
FIG. 1 shows an overview of a prior art SPIM arrangement for imaging samples.

FIG. 1 illustrates the fundamental principles of SPIM and described more extensively in U.S. Pat. No. 7,554,725, the disclosure of which is incorporated by reference. The arrangement 10 comprises a laser 20, which generates, through an illumination objective 25, a light sheet 30 to illuminate sections of a sample 40. The light sheet 30 is directed along an illumination beam path 35. A detection objective 65 is arranged such that the detection direction 55 is substantially orthogonal to the plane of the light sheet 30 (i.e. perpendicular to the illumination beam path 35).

The sample 40 can be rotated about a rotation axis 45 and the light sheet 30 can be arranged to illuminate optical sections of the sample 40. The laser 20 typically excites fluorophores in the sample 40 to emit fluorescent light in many directions.

The detector 50 detects, through an detection objective 65 and optical arrangement 66, a portion of the emitted fluorescent light from the fluorophores in the sample 40 that have been excited by the radiation in the light sheet 30. The detector 50 has an imaging device 60, such as a CCD camera, that is connected to a processor 70 with a memory store 80. The memory store 80 stores the individual images 85 from each of the optical sections of the sample 40 and the processor 70 can create a three dimensional image of the sample 40.

Figure 2:
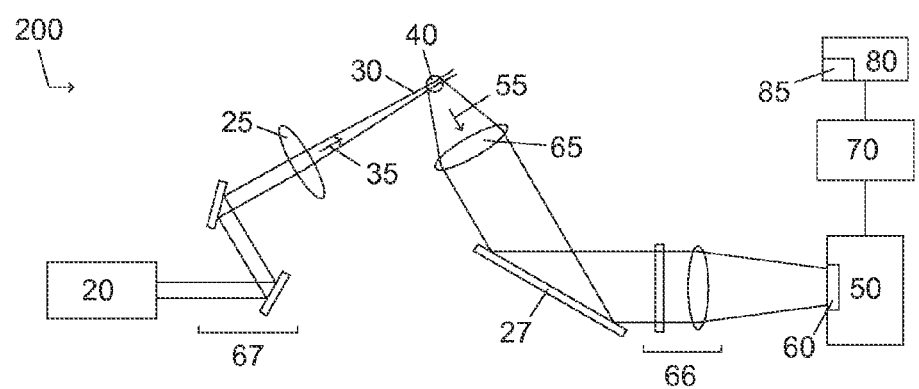
FIG. 2 shows an overview of the SPIM arrangement used in one aspect of this disclosure.

FIG. 2 shows an embodiment of the microscope arrangement 200 used in this disclosure. Identical reference numerals are used to indicate identical elements in FIGS. 1 and 2. There is no need to embed the sample 40 in agarose in this disclosure, since the sample 40 is held sufficiently stable in the apparatus, as will be explained below.

The laser 20 generates through mirrors 67 and illumination objective 25 a light sheet 30 to illuminate sections of sample 40. The light sheet 30 enters the sample 40 through the lower surface of the sample 40. A large portion of the emitted fluorescent light from the sample 40 is passed through a detection objective 65, reflected by a mirror 27 and through the optical arrangement 66 focussed onto the imaging device 60 in the detector 50 to form an image. The image from the detector 50 is passed to the processor 70 and then stored in the memory store 80 as individual images 85.

Figure 3:
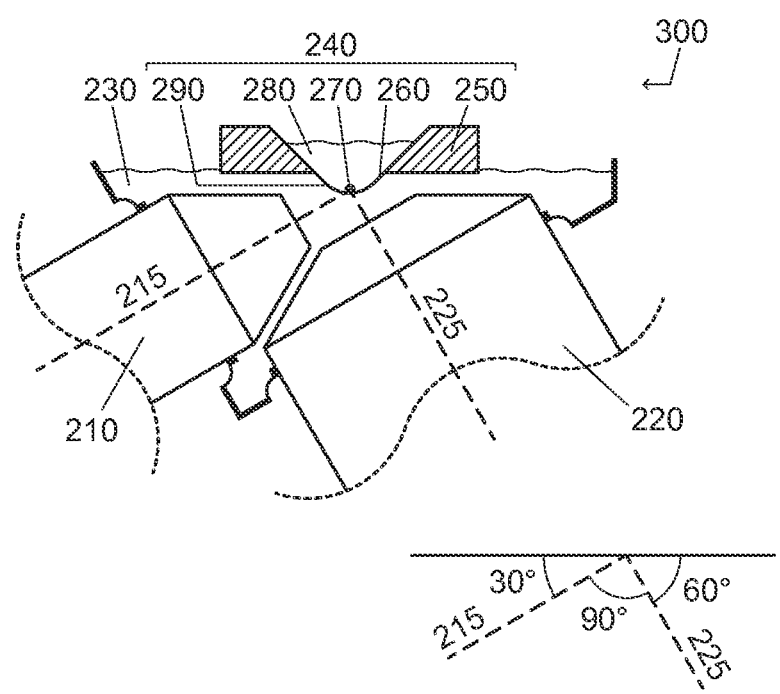
FIG. 3 shows an overview of a microscope module.

FIG. 3 shows an example of the microscope module 300 with an illumination objective 210 and a detection objective 220. The illumination objective 210 illuminates by an illumination beam (light sheet) along an illumination beam path 215. The illumination beam path 215 through the illumination objective 210 and a detection path 225 through the detection objective 220 are arranged approximately orthogonal to each other. Both the illumination objective 210 and the detection objective 220 are located in an immersion medium 230, which comprises typically degassed water or immersion oil. Degassing of the water ensures that bubbles are not present in the immersion medium 230.

The illumination beam path 215 through the illumination objective 210 is located beneath a sample holder 240 at approximately 30° to the plane of the sample holder 240. The detection path 225 is therefore located at approximately 60° to the plane of the sample holder 240. Flexible plastic rings around the illumination objective 210 and the detection objective 220 prevent leakage of the immersion medium 230.

The sample holder 240 with walls 250 is made of a biocompatible material, such as but not limited to PEEK, and has a bottom 260 that is made of a thin transparent membrane, such as a Teflon® FEP film manufactured by Dupont, having a refractive index substantially similar to that of the immersion medium 230 and/or the culture medium 280 to reduce optical aberrations. The transparent membrane in the bottom 260 allows therefore the passage of radiation onto a sample 270 located on the top side of the transparent membrane 260. The transparent membrane forming the bottom 260 is attached to the walls 250 of the sample holder 240 by biocompatible silicone glue or by clamping. The transparent membrane is curved in the area not supported by the walls 250 to keep the transparent membrane under tension. The sample holder 240 is open at the top and the opening enables easy access to and removal of the sample 270, if required. The transparent membrane is plasma treated to make it hydrophilic and thus helps to prevent bubble formation in the immersion medium 230.

The sample 270 is located in the curved area in the transparent membrane in a suitable culture medium 280. The culture medium 280 is an embryo or tissue culture medium and may have a layer of oil on its surface to prevent evaporation. The different refractive index of the oil will not affect the imaging of the sample 270 because the illumination beam path 215 and/or the detection path 225 do not pass through the oil. The culture medium 280 may have a very small volume, for example 10 µl. Examples of such culture media 280 include, but are not limited to, KSOM, M16 (mouse embryo), DMEM and RPE (cell culture). There is no need to embed the sample 270 in an agarose cylinder (as known in the art). The protrusion 290 can be elongated to form a trough (see FIG. 4).

The microscope module 300 shown in FIG. 3 enables the isolation of the immersion medium 230 from the culture medium 280. It can be seen that this is different than the arrangement 10 of FIG. 1 in which the immersion medium is the same as the aqueous medium holding the sample 40.

The sample 270 can also be easily manipulated as the sample 270 is accessible from the top side through the culture medium 280. An opening in the sample holder 240 allows access to the sample 270.

It will be seen from the arrangement of FIG. 3 that only the lower surfaces, including bottom surface and side surfaces, of the sample 270 will be illuminated by the radiation from the illumination objective 210. Similarly the fluorescent light from the lower surfaces of the sample 270 will be collected by the detection objective 220 and thus used to create the image 85 in the memory store 80.

Figure 4:
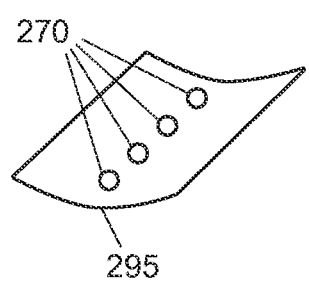
FIG. 4 shows an elongated trough in which the samples are placed.

The protrusion 290 can be in the form of an elongated trough 295, as shown in FIG. 4. This aspect of the invention allows multiple ones of the samples 270 to be placed along the trough and imaged using the same microscope module 300. Such an arrangement will allow high throughput imaging of a plurality of the samples 270.

The microscope module 300 enables long-term high-throughput live cell and embryo imaging experiments, for example, of mammalian embryos and oocytes imaged in vitro.

A method for carrying out long-term high-throughput live cell and embryo imaging experiments can be carried out by the microscope module 300. The method comprises arranging the illumination objective 210 such that an illumination beam is produced to illuminate the lower surfaces of the plurality of samples 270 along the illumination beam path 215. The detection objective 220 collects a portion the fluorescent light that is emitted from the plurality of samples 270. The fluorescent light is emitted in all directions and fluorescent light in an arc of approx. 120° about the detection path 225 will be collected. The fluorescent light collected by the detection objective 220 is reflected by a mirror 27 and through the optical arrangement 66 focussed onto the imaging device 60 in the detector 50. The imaging device 60 sends to the processor 70 data relating to the images 85 and the processor 70 is able to create a three-dimensional image of one or more of the plurality of samples 270.

It will be seen from FIG. 4 that the elongated trough 295 can be moved so that the detection objective 220 and the illumination objective 210 scan the elongated trough 295 to image different ones of the plurality of the samples 270. The detection objective 220 and the illumination objective 210 remain fixed to an optical table.

The culture medium 280 remains undisturbed by either of the detection objective or of the illumination objective and remains sterile allowing long-term experiments.

REFERENCE NUMERALS

10 Arrangement
20 Laser
25 Illumination objective
27 Mirror
30 Light sheet
35 Illumination beam path
40 Sample
45 Rotation axis
50 Detector
55 Detection direction
60 Imaging device
65 Detection objective
66 Optical arrangement
67 Mirrors
70 Processor
80 Memory store
85 Images
200 Microscope arrangement
210 Illumination objective
215 Illumination beam path
220 Detection objective
225 Detection path
230 Immersion medium
240 Sample holder
250 Walls
260 Bottom
270 Sample
280 Culture medium
290 Protrusion
295 Trough
300 Microscope module

The invention claimed is:

1. A microscope module for a microscope arrangement for imaging a sample, the microscope arrangement comprising:
    a light source for generating an illumination beam along an illumination beam path; and
    a detector for detecting emitted light along a detection beam path;
wherein the microscope module comprises:
    a sample holder, removably arranged in the microscope arrangement and adapted for holding the sample on top of the sample holder, and having a bottom transparent to the illumination beam and light emitted from the sample;
    at least one illumination objective, located below the sample holder and arranged in the microscope arrangement to direct the illumination beam through the bottom of the sample holder; and
    at least one detection objective, located below the sample holder and arranged in the microscope arrangement to collect the light emitted from the sample through the bottom of the sample holder along the detection path;
    wherein the illumination objective and the detection objective are located in an immersion medium in contact with the at least partially transparent bottom of the sample holder.

2. The microscope module according to claim 1, wherein the angle of the detection path to the illumination beam path is substantially orthogonal.

3. The microscope module according to claim 1, wherein a refractive index of the immersion medium is substantially similar to a refractive index of the at least partially transparent bottom of the sample holder.

4. The microscope module according to claim 1, wherein the at least partially transparent bottom of the sample holder is made of a membrane.

5. The microscope module according to claim 1, wherein the sample is in a culture medium.

6. The microscope module according to claim 5, wherein the culture medium has a refractive index substantially similar to that of the at least partially transparent bottom of the sample holder.

7. The microscope module for a microscope arrangement for imaging a sample, the microscope arrangement comprising:
    a light source for generating an illumination beam along an illumination beam path; and
    a detector for detecting emitted light along a detection beam path;
wherein the microscope module comprises:
    a sample holder, removably arranged in the microscope arrangement and adapted for holding the sample on top of the sample holder, and having a bottom transparent to the illumination beam and light emitted from the sample;
    at least one illumination objective, located below the sample holder and arranged in the microscope arrangement to direct the illumination beam through the bottom of the sample holder; and
    at least one detection objective, located below the sample holder and arranged in the microscope arrangement to collect the light emitted from the sample through the bottom of the sample holder along the detection path,
    wherein the at least partially transparent bottom of the sample holder comprises a protrusion in which the sample is held.

8. The microscope module according to claim 7 wherein the illumination beam is arranged to illuminate the sample through a bottom of the protrusion.

9. The microscope module according to claim 8 wherein the protrusion is elongated.

10. The microscope module according to claim 1, wherein the illumination beam path is arranged at substantially 30° to horizontal.

11. A method of imaging one or more samples comprising:
    placing one or more samples onto a top of a sample holder with a partially transparent bottom;
    removably arranging the sample holder above an illumination objective and a detection objective, wherein the illumination objective and the detection objective are located in an immersion medium in contact with the at least partially transparent bottom of the sample holder;
    passing light from a light source through the illumination objective;
    illuminating through the partially transparent bottom of the sample holder the one or more samples with the illumination beam;
    detecting with the detection objective emitted light from the one or more samples through the partially transparent bottom of the sample holder; and
    creating an image of the one or more samples.

12. The method according to claim 11, further comprising selecting different ones of the one or more samples.

13. A microscope module for a microscope arrangement having a light source for generating an illumination beam along an illumination beam path and a detector for detecting emitted light along a detection beam path, the microscope module comprising:
- a sample holder, removably arranged in the microscope arrangement and adapted for holding the sample on top of the sample holder, and having a bottom transparent to the illumination beam and light emitted from the sample;
- at least one illumination objective, located below the sample holder and arranged in the microscope arrangement to direct the illumination beam through the bottom of the sample holder; and
- at least one detection objective, located below the sample holder and arranged in the microscope arrangement to collect the light emitted from the sample through the bottom of the sample holder along the detection path;
- wherein the illumination objective and the detection objective are located in an immersion medium in contact with the at least partially transparent bottom of the sample holder.

* * * * *